(12) United States Patent
Galli et al.

(10) Patent No.: US 10,420,998 B2
(45) Date of Patent: Sep. 24, 2019

(54) PROCESS AND SYSTEM FOR MEASURING OR PREDICTING A HURDLE RACE TIME

(71) Applicant: SWISS TIMING LTD., Corgemont (CH)

(72) Inventors: Reto Galli, Munchenbuchsee (CH); Pascal Richard, Corgemont (CH)

(73) Assignee: SWISS TIMING LTD, Corgemont (CH)

( * ) Notice: Subject to any disclaimer, the term of this patent is extended or adjusted under 35 U.S.C. 154(b) by 528 days.

(21) Appl. No.: 15/246,621

(22) Filed: Aug. 25, 2016

(65) Prior Publication Data

US 2017/0065864 A1    Mar. 9, 2017

(30) Foreign Application Priority Data

Sep. 3, 2015    (EP) .................................... 15183712

(51) Int. Cl.
| | | |
|---|---|---|
| *A63B 24/00* | (2006.01) | |
| *A63B 69/00* | (2006.01) | |
| *G07C 1/22* | (2006.01) | |
| *A61B 5/11* | (2006.01) | |

(Continued)

(52) U.S. Cl.
CPC ............ *A63B 69/0028* (2013.01); *A61B 5/11* (2013.01); *A63B 24/0003* (2013.01); *G07C 1/22* (2013.01); *A61B 2503/10* (2013.01); *A63B 2220/40* (2013.01); *A63B 2220/803* (2013.01); *A63B 2220/836* (2013.01); *A63B 2225/54* (2013.01); *A63B 2244/088* (2013.01); *A63K 3/043* (2013.01); *G01P 15/00* (2013.01)

(58) Field of Classification Search
CPC ..... A63B 24/0062; A63B 69/00; G01P 15/00; A63K 3/043
See application file for complete search history.

(56) References Cited

U.S. PATENT DOCUMENTS

| 2006/0136173 A1* | 6/2006 | Case, Jr. ................ A63B 24/00 |
| | | 702/182 |
| 2008/0249736 A1* | 10/2008 | Prstojevich ............ A61B 5/112 |
| | | 702/141 |

(Continued)

FOREIGN PATENT DOCUMENTS

| CH | 707 401 A2 | 6/2014 |
| EP | 1 992 389 A1 | 11/2008 |

(Continued)

OTHER PUBLICATIONS

European Search Report for EP 15 18 3712 dated Mar. 2, 2016.

*Primary Examiner* — Steven J Hylinski
(74) *Attorney, Agent, or Firm* — Sughrue Mion, PLLC

(57) ABSTRACT

The process enables a time of an athlete in a hurdle race to be measured or predicted with a personalized transponder module positioned on the athlete and a base station. The transponder module comprises a receiver unit, a processing unit, a transmitter unit for data signals and a motion sensor to supply measurement signals to the processing unit. The module is activated by a wake-up signal and a measurement of the movement is conducted by the sensor after the start of the race on passage of each hurdle. The data signals are transmitted to the base station and determination of a passage time over each hurdle is conducted.

16 Claims, 3 Drawing Sheets

(51) Int. Cl.
*G01P 15/00* (2006.01)
*A63K 3/04* (2006.01)

(56) References Cited

U.S. PATENT DOCUMENTS

| | | | | |
|---|---|---|---|---|
| 2013/0274904 A1* | 10/2013 | Coza | ........................ | G06F 3/011 |
| | | | | 700/91 |
| 2014/0180595 A1* | 6/2014 | Brumback | ............ | A61B 5/0015 |
| | | | | 702/19 |
| 2014/0213382 A1* | 7/2014 | Kang | .................. | A63B 69/3632 |
| | | | | 473/223 |
| 2014/0326084 A1* | 11/2014 | Bhushan | ................... | A61B 5/11 |
| | | | | 73/865.4 |
| 2015/0272484 A1* | 10/2015 | Ronchi | ................. | A61B 5/4595 |
| | | | | 600/595 |
| 2017/0046979 A1* | 2/2017 | Lehary | ................. | H04B 1/3888 |

FOREIGN PATENT DOCUMENTS

| | | |
|---|---|---|
| EP | 2 654 030 A1 | 10/2013 |
| WO | 2011/085501 A1 | 7/2011 |

* cited by examiner

PROCESS AND SYSTEM FOR MEASURING OR PREDICTING A HURDLE RACE TIME

This application claims priority from European Patent Application No. 15183712.7 filed on Sep. 3, 2015, the entire disclosure of which is hereby incorporated herein by reference.

FIELD OF THE INVENTION

The invention relates to a process for measuring or predicting a hurdle race time in athletics.

The invention also relates to a system for measuring or predicting a hurdle race time in athletics for implementing the process.

BACKGROUND OF THE INVENTION

In an athletics sprint race, such as a hurdle race, it is very important to be highly efficient during the race, particularly when crossing each hurdle. In particular, the hurdle race can be a 60 m, 100 m, 110 m or 400 m race. Clearance or passage of each hurdle is technically difficult and demands good coordination of the movement of the legs of the athlete to be the fastest for the entire duration of the race. Thus, during training the passage time over each hurdle can be an important parameter. There are already hurdles equipped with sensors, e.g. integrated into a section of the hurdle in order to detect the passage of the athlete for this purpose. For simplification, the measurement of the time is conducted manually by the trainers by frequently taking the time when a leg of the athlete touches the ground after passage of the hurdle. There exist tables with the optimum times for crossing each hurdle to define a given finish time of the athlete.

Patent application TW 201134517 A describes an analysis system for a hurdle race. The system comprises several hurdles arranged on a ring-shaped track, several detection devices and an analysis device. Each detection device comprises an approach sensor, a vibration sensor and a touch-sensitive sensor. When the athlete runs and jumps a hurdle, the approach sensor sends a passage signal. When the athlete hits a hurdle lightly, the vibration sensor sends a vibration signal. When the athlete hits the hurdle heavily and it falls, the touch-sensitive sensor sends a contact signal. The analysis device can then calculate the time between two successive hurdles, the race speed and the fault times for training references. There is no provision for controlling or predicting a race time on passage of each hurdle in order to determine the position and estimated time of each racing athlete, which constitutes a drawback.

In a 400 m hurdle race, for example, this race begins on a bend, which makes it difficult for spectators to see each athlete and know which athlete is ahead in the race before seeing them on each straight section of the race track. There is no possibility of supplying the passage time over each hurdle in real time during a race. Knowing or estimating the passage time over each hurdle may make it possible to predict what the final race time of each athlete will be.

According to the prior art, it is not known to estimate or predict a time of each athlete in such a hurdle race on the basis of optimum times, in particular after passage of two or three hurdles. With this, it would also be possible to determine a position of each athlete in order to know which athlete is ahead in the race, in particular in a 400 m hurdle race, which is sought in the present invention.

SUMMARY OF THE INVENTION

Therefore, the aim of the invention is to remedy the drawbacks of the abovementioned prior art by proposing a process for measuring or predicting a hurdle race time in athletics, in which it is possible to estimate and predict the final time of a hurdle race and allow it to be known simply which athlete is ahead in the race.

For this, the invention relates to a process for measuring or predicting a time in a hurdle race of at least one athlete by means of a personalized transponder module positioned on the athlete and a base station of a measurement system, wherein the transponder module comprises at least a signal receiver unit, a processing unit for data, measurements or commands, a transmitter unit for data and/or measurement and/or command signals, and at least one motion sensor to supply measurement signals to the processing unit, the process being wherein it comprises the following steps:
- activating the personalized transponder module following the receipt of a wake-up signal in the receiver unit,
- measuring at least one variation in movement of the athlete by the motion sensor on passage of one or more hurdles during the race,
- transmitting measurement signals directly or formatted with determination of variations in movement in the processing unit by the transmitter unit to the base station, and
- determining a passage time of the athlete over one or more hurdles by one or more measurements of variations in movement of the motion sensor.

Particular steps of the process for measuring or predicting a hurdle race time in athletics are defined in the dependent claims 2 to 11.

An advantage of the measurement process lies in the fact that with the transponder module placed on a part of the athlete's body, it is possible to determine or estimate the passage time of each hurdle on the race track in real time. It is thus possible in the base station in particular by receipt of data or measurement signals from the transponder module to show to the spectators which athlete is ahead in the race and in particular in a 400 m hurdle race.

Advantageously, the measurement or prediction process enables the finish time of each athlete in the race to be predicted on the basis of the passage of the preceding hurdles. For high-level hurdle races, it can be assumed that the athletes run at an optimum in view of their racing frequency. After only passage of two or three hurdles, it is already possible to determine whether a potential record of one of the racing athletes can be expected.

For this, the invention also relates to a system for measuring or determining a time in a hurdle race of an athlete for implementing the measurement process, wherein the measurement system comprises at least one a personalized transponder module positioned on an athlete and a base station, wherein said transponder module comprises at least a signal receiver unit, a processing unit for data, measurements or commands, a transmitter unit for data and/or measurement and/or command signals, and at least one motion sensor to supply measurement signals to the processing unit, wherein the transponder module is configured to be woken up by a wake-up signal received by the receiver unit in order to enable the motion sensor to measure one or more variations in movement of the athlete on passage of one or more hurdles during the race, and in that the base station or the processing unit is arranged to determine a passage time over the hurdle or hurdles during the race.

Particular embodiments of the system for measuring or predicting a hurdle race time in athletics are defined in the dependent claims 13 to 15.

BRIEF DESCRIPTION OF THE DRAWINGS

The aims, advantages and features of the process and system for measuring or predicting a hurdle race time in athletics according to the invention will become clearer in the following description of at least one non-restrictive embodiment illustrated by the drawings.

DETAILED DESCRIPTION OF THE INVENTION

In the following description all those elements of the system for measuring or predicting a hurdle race time in athletics for implementation of the measurement process that are well known to a person skilled in the art in this technical field will only be explained in a simplified manner.

Figure 1:
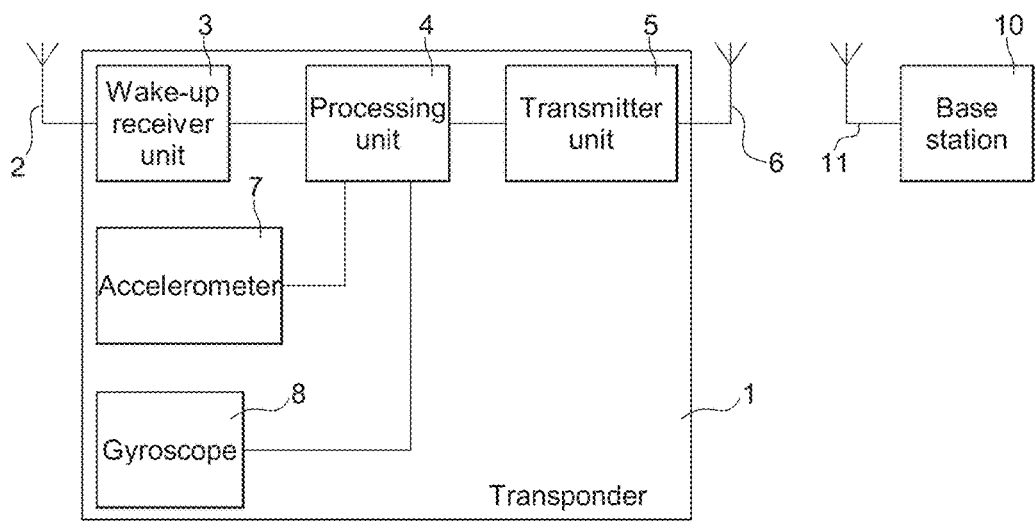
FIG. 1 schematically shows the main elements of a system for measuring or predicting a hurdle race time in athletics according to the invention.

FIG. 1 schematically shows the main elements that make up a system for measuring or predicting a hurdle race time in athletics. For this, the system comprises one or more transponder modules or circuits 1 and at least one base station 10 for the communication of data and/or measurements and/or commands between the transponder modules or circuits 1 and the base station 10. Each transponder module 1 for the competition is arranged on a part of the body of an athlete, e.g. in a race bib, and is therefore personalized to the athlete who wears it. The transponder module 1 is preferably arranged on an upper part of the athlete's body at the level of his/her centre of gravity such as the chest in order to detect the rotation of the upper body of the athlete for determining and predicting a hurdle race time.

The transponder module 1 can be active with a solar battery or cell integrated into the module or passive being supplied by the receipt of a traditional interrogation signal.

The transponder module or circuit 1 comprises a wireless signal receiver unit 3 to receive via an antenna 2 data or command signals 3 coming from a base station 10 or an emitter arranged in a starting block of the measurement system or along a race track. The base station 10 can be the timing system of the race and comprises an antenna 11 for transmitting or receiving signals. The signals received by the antenna 2 linked to the receiver unit 3 are preferably signals that enable the transponder module 1, which is in a resting state before receipt of such signals, to be woken up. As indicated above, these wake-up signals are generated by the base station 10 or by an emitter of the starting block or along the race track. These wake-up signals are generated, for example, after the preparation signal for the start of an athletics race in particular or directly at the instant the starting gun is fired. The gun can be an electronic gun or a powder gun with a transducer and can also be part of the measurement system. These wake-up signals can also be generated after the start of the race before passage or clearance of a first hurdle, but in this case a synchronisation of the transponder module 1 may be necessary.

The transponder module 1 also comprises a processing unit 4, which can be a state machine, a processor or a microcontroller for management of all the data or commands or measurements to be received or transmitted. The processing unit 4 receives the data or commands formatted in the receiver unit 3 to also wake up all the components that make up the transponder module 1. The processing unit 4 is also connected to a signal transmission unit 5 by an antenna 6 for transmission to the base station 10, which can be the timing system.

The transponder module 1 also comprises at least one motion sensor 7, 8 connected to the processing unit 4 to supply measurement signals either continuously or intermittently to the processing unit 4 once the transponder module has woken up. The transponder module 1 can comprise an accelerometer 7 and/or a gyrometer or gyroscope 8 as motion sensor. An accelerometer 7 is preferably provided to measure the acceleration or variations in movement of an athlete when clearing each hurdle of the race and a gyroscope 8 to determine a speed or direction of rotation and an angle of rotation of the upper part of the body of the athlete. With this measurement of rotation of the transponder module 1 placed on the upper part of the athlete's body, it is possible to determine the clearance or passage of each hurdle, since the angle of rotation before and after passage of the hurdle is the reverse. The measurement signals are supplied directly to the processing unit 4.

The accelerometer 7 used can be an accelerometer with one, two or three measurement axes to supply a measurement signal relating to one or more variations in movement of said module during the race and on passage of the hurdles. These variations in movement can relate to the shocks of a foot of an athlete received on the ground after passage of each hurdle, which corresponds to a vertical acceleration. This must be detected differently from the normal acceleration of the racing stride of each athlete. Thus, beyond a certain defined acceleration threshold or a certain threshold of variations in movement, it is possible to use this measurement of the accelerometer to precisely determine the passage time of each hurdle. Variations in movement over a measurement period can also be taken into consideration by taking the flight time over each hurdle crossed during the race into consideration.

The gyroscope 8 can also be a gyroscope with one, two or three measurement axes and form a detection assembly with the accelerometer to supply a measurement signal relating to the speed or direction of rotation of the upper body of the athlete and the angle of rotation on passage of each hurdle.

The measurement signals of the accelerometer 7 and the gyroscope 8 or other types of sensors are sampled by the processing unit 4. The measurement signals can be transmitted directly to the base station 10 using the wireless transmitter unit 5. However, the measurement signals can be improved in particular after filtering and then stored and/or sent subsequently to the base station 10 after processing. It can also be provided to process the data of different sensors and any detection event such as a jump. It can further be provided to process the movement characteristics extracted, such as the pace frequency, and transmit this information to the base station 10 in addition to the actual data of the accelerometer 7 and the gyroscope 8.

Figure 2:
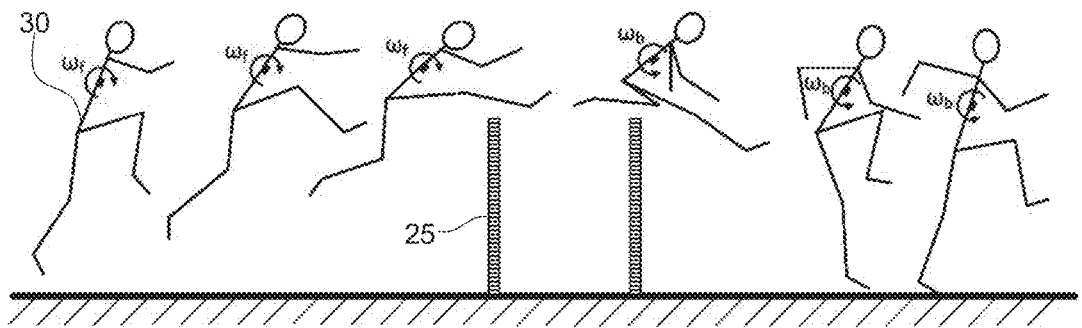
FIG. 2 shows a racing athlete in different phases of jumping a hurdle of the measurement process according to the invention.

It should be noted that the transponder module 1, which comprises the accelerometer and the gyroscope can be identical to that described in patent application EP 2 747 036 A1 in paragraphs 32 to 37 in relation to FIG. 2 of the patent application, which is incorporated herein by reference. A synchronisation of the transponder module 1 can be conducted from the start of the race in order to determine the hurdle passage times following the measurements conducted by the motion sensors directly in the transponder module before transmission of data signals to the base station.

It should also be noted that the signals received by the antenna 2 linked to the receiver unit 3 can be signals at low frequency in the order of 125 kHz, while the signals transmitted by the antenna 6 linked to the transmitter unit 5 can be UHF signals at a frequency ranging between 300 MHz and 3000 MHz. However, it can be conceivable to have a transponder module 1 with a single switchable receiver and emitter antenna for receipt or emission of data signals. In this scenario, it is preferable to have a receipt of at least one wake-up signal and an emission of data signals at a similar carrier frequency with an FSK, BPSK, QPSK or ON-OFF keying modulation of the transmitted data.

To be efficient in a hurdle race, the athlete must keep his/her centre of gravity as low as possible during each hurdle jump. To do this, the athlete must bend forwards during the jump, as can be seen in the different positions of the athlete 30 for passage of a hurdle 25 in FIG. 2. The highest point of the jump is when the athlete 30 draws his/her trailing leg over the hurdle 25 and he/she would thus be bent forward to the maximum degree. In a jump close to the optimum, this also corresponds to the instant the centre of gravity passes over the hurdle.

Thus, as motion sensor, the gyroscope measures a forward rotation ωr before the athlete 30 passes the hurdle 25, as shown by the first three positions of the athlete 30 on passage of the hurdle 25, and a backward rotation ωb after passage of the hurdle 25 with the second three positions of the athlete 30, which following the first three positions. With this change of sign of the direction of rotation on passage of each hurdle, it is possible to determine a passage time by this change of sign from the measurement signals supplied by the gyroscope of the transponder module.

In the raw signal of the gyroscope, the change of sign of the rotation can be used to define the exact passage over the hurdle 25 of each racing athlete 30. If the signal of the gyroscope is integrated to obtain the absolute angle of inclination of the upper part of the body of the athlete 30, the maximum angle defines the passage of the hurdle.

Figure 3:
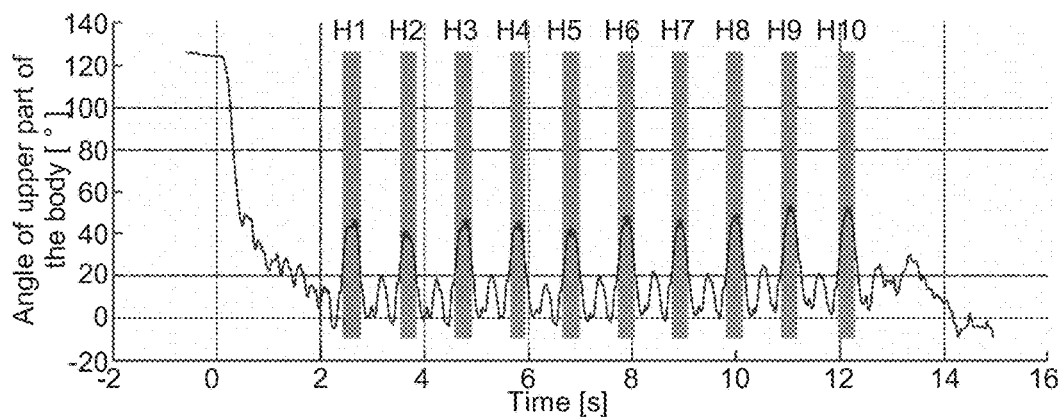
FIG. 3 is a graph showing the time of inclination of the upper part of the body of the athlete wearing the transponder module during a 100 m hurdle race of the measurement process according to the invention.

FIG. 3 shows the inclination of the upper part of the athlete's body with maximum values directly above each hurdle to determine the passage of each hurdle. The maximum values are shown in each grey rectangle in FIG. 3 with indications H1, H2, H3, H4, H5, H6, H7, H8, H9 and H10 of the hurdles of the race. This graph relates to a 100 m hurdle race.

Figure 4:
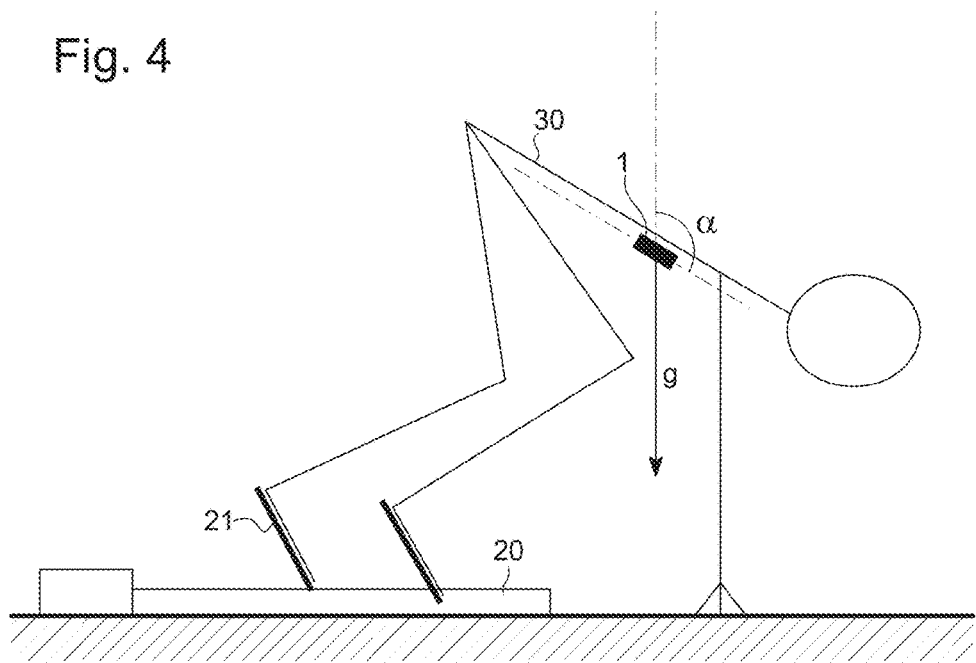
FIG. 4 schematically shows an athlete who is fitted with a transponder module in starting position on a starting block according to the invention.

To make an estimation of the inclination of the upper part of the athlete's body as shown in FIG. 3, it is necessary to know the initial angle at the start of the race. This angle α can be estimated by measuring the gravity vector g during the preparation phase of the athlete in a crouched position on the starting block 20, for example, as shown in FIG. 4. The time of the starter's command to get ready and the start signalled by the starting gun are also taken into consideration.

FIG. 4 thus schematically shows the athlete 30 at the instant of the start of the hurdle race. The athlete's 30 two feet are resting against two blocks 21 of a starting block 20 placed and fixed in position on the ground of the race track. The athlete 30 is fitted with a preferably active transponder module 1. The transponder module 1 is fitted with at least one motion sensor, and preferably two motion sensors such as the accelerometer and the gyroscope.

Tests with athletes show that a precision in the order of ±0.02 s can be achieved for the passage time over each hurdle. A higher precision is achieved with the contact time of the leg on the ground after passage of the hurdle, i.e. as soon as one foot touches the ground after the hurdle. This can be easily detected by evaluating the vertical acceleration caused by the contact with the ground after passage of the hurdle and by being measured by the accelerometer of the transponder module. The contact with the ground on landing from a hurdle jump can be distinguished from a contact with the ground on each normal racing stride by the flight time which precedes the contact with the ground. Although the measurement of the time for the contact with the ground is more precise than the measurement of the passage time over the hurdle, it is not better suited to defining a placing, since the position of the contact with the ground can vary between athletes.

Figure 5:
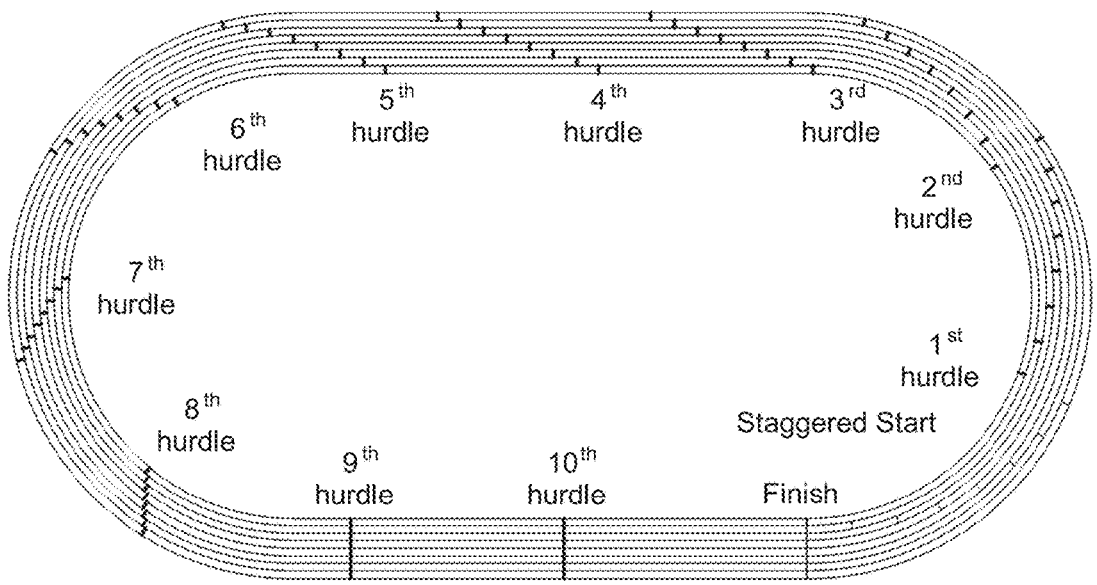
FIG. 5 schematically shows different positions on the track of a 400 m hurdle race for the measurement process according to the invention.

For applications that use the passage time of the hurdles, the first eight hurdles in FIG. 5 in a 400 m hurdle race are sampled. The distances between the start and the first hurdle and between the last hurdle and the finish are equal, and this applies for all the race lanes. With this sampling of hurdle placement it is very difficult to see who is ahead in such a race. Moreover, there is not a simple way of creating an automatic placing before the athletes are on the straight section of the track before the finish. According to the process of the invention by having the time at each hurdle or the contact time on the ground after each hurdle, it is possible to create a placing in real time and show this information to the spectators on a screen.

Figure 6:
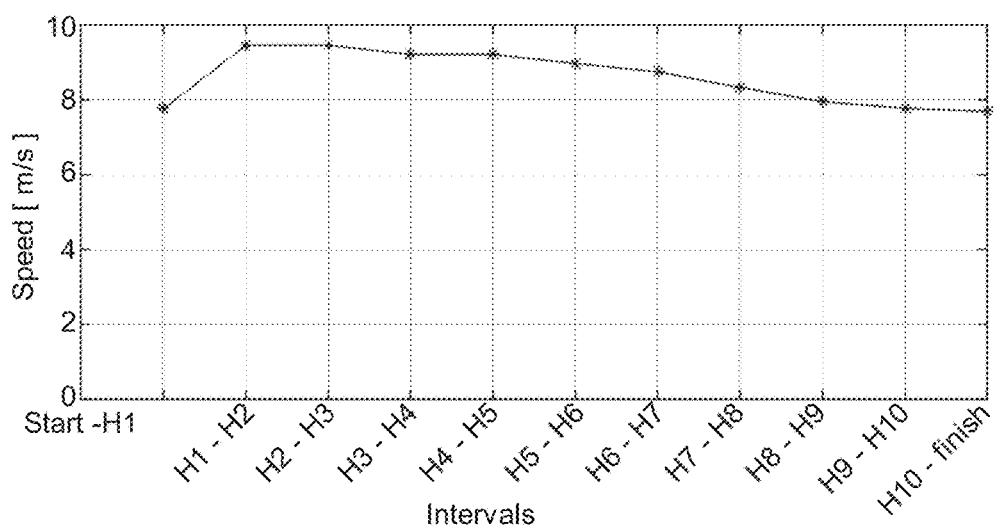
FIG. 6 shows a graph of the speed of the athlete between each interval of a 400 m hurdle race where the references of the intervals are also shown in FIG. 3 of a 100 m hurdle race for the measurement process according to the invention.

The distance between two successive hurdles is precisely defined in the international competition rules for each type of race. This can be 8.5 m for a 100 m hurdle race, 9.14 m for a 110 m race and 35 m for a 400 m race. By determining the time for passage of each hurdle, it is possible to calculate the average speed for each race segment, i.e. between the hurdles of the race, and create a speed profile. FIG. 6 shows a representation of just such a speed profile for a 400 m hurdle race. The same indications H1, H2, H3, H4, H5, H6, H7, H8, H9 and H10 of the 100 m hurdle race described with reference to FIG. 3 are used again in the graph of FIG. 6 to define the race intervals. The graph of this FIG. 6 thus defines a speed for each race interval.

In a 100 m or 110 m hurdle race, an athlete takes 3 steps between two successive hurdles. This is only possible with a steady pace in a movement model. Acceleration between the hurdles is difficult to achieve in these conditions. Elite hurdlers train to maintain the pace and therefore do not slow down. Such a hurdle race consists of an acceleration phase between the start and the first hurdle, then a largely constant speed over all the hurdles is established and there can be another slight acceleration at the end between the last hurdle and the finish. Thus, with the time over the first four hurdles passed, it is possible to predict the time over the last hurdle absolutely precisely at ±0.05 s, using a linear extrapolation. The possible acceleration after the last hurdle may not change the final time of an elite athlete with an error of +0.05 s/−0.1 s, but on the condition that the athlete finishes the race normally, i.e. that the athlete does not trip, for example. This would enable a potential new record to be announced on the results screen, the TV screen or to commentators before the race finishes.

On the basis of the description just given, several variants of the process and system for measuring or predicting a hurdle race time in athletics can be imagined by a person skilled in the art without departing from the framework of the invention as defined by the claims. The transponder module can comprise several other sensors, such as a temperature sensor, for example. One or more transponder modules can be arranged in other locations than on the upper body of the athlete.

What is claimed is:

1. A process for measuring or predicting a time in a hurdle race of at least one athlete by means of a personalised transponder module positioned on the athlete and a base station of a measurement system, wherein the transponder module comprises at least a signal receiver unit, a processing unit for data, measurements or commands, a transmitter unit for data and/or measurement and/or command signals, and at least one motion sensor to supply measurement signals to the processing unit,
   wherein the process comprises the following steps:
      activating the personalised transponder module following the receipt of a wake-up signal in the receiver unit,
      measuring at least one variation in movement of the athlete by the motion sensor on passage of one or more hurdles during the race,
      transmitting measurement signals directly or formatted with determination of variations in movement in the processing unit by the transmitter unit to the base station,
      determining a passage time of the athlete over one or more hurdles by one or more measurements of variations in movement of the motion sensor, and
      during the hurdle race, predicting at least one of a placing of the athlete and a final race time of the athlete.

2. The measurement process according to claim 1, in which the motion sensor is an accelerometer with one, two or three measurement axes, wherein after having activated the transponder module by the wake-up signal, the accelerometer measures one or more variations in acceleration or movement of the athlete on passage of one or more hurdles during the race, and in that the transmitter unit transmits the measurement signals supplied by the processing unit directly to the base station, or data signals on the basis of the determination of the variations in acceleration or movement in the processing unit to determine at least one passage time of the hurdle or hurdles passed.

3. The measurement process according to claim 2, wherein the determination of a passage time of each hurdle is obtained by a measurement of the variation in acceleration or movement following the received contact of a foot of an athlete on the ground after passage of each hurdle.

4. The measurement process according to claim 1, in which the transponder module is arranged on an upper part of the body of the athlete and in which the motion sensor is a gyroscope with one, two or three measurement axes, wherein after having activated the transponder module by the wake-up signal, the gyroscope measures a speed or a direction of rotation of the transponder module on the athlete on passage of one or more hurdles to determine at least one passage time of the hurdle or hurdles passed, and in that the transmitter unit transmits the measurement signals supplied by the processing unit directly to the base station, or formatted in the processing unit on the basis of the measurement of the speed or direction of rotation of the transponder module on the athlete on passage of the hurdle.

5. The measurement process according to claim 4, wherein the processing unit takes into consideration the change in direction of rotation in the measurement signals of the gyroscope for determination of a passage time over each hurdle during the race.

6. The measurement process according to claim 1, in which the transponder module is arranged on an upper part of the body of the athlete and in which the transponder module comprises two motion sensors, which are an accelerometer with one, two or three measurement axes and a gyroscope with one, two or three measurement axes, wherein after having activated the transponder module by the wake-up signal, the accelerometer measures one or more variations in acceleration or movement of the athlete on passage of one or more hurdles during the race, and in that the gyroscope measures a speed or direction of rotation of the transponder module on the athlete on passage of one or more hurdles on the athlete, and in that the transmitter unit transmits the measurement signals of the accelerometer and the gyroscope supplied directly or formatted by the processing unit to the base station for determination of a passage time over each hurdle during the race.

7. The measurement process according to claim 1, wherein the wake-up signal is received by the receiver unit of the transponder module to activate it from the base station or an emitter at a race starting point or at a point of the race track of the athlete at the instant of a starting signal generated by a starting gun shot of the measurement system.

8. The measurement process according to claim 2, wherein after having activated the transponder module by the wake-up signal, the accelerometer or the gyroscope or the accelerator and the gyroscope supply measurement signals to the processing unit to determine directly in the processing unit a passage time over each hurdle during the race on the basis of a threshold of variations in movement or rotation speed of the transponder module or a change in the direction of rotation of the transponder module before transmitting the data signals to the base station for determination of a passage time over each hurdle during the race.

9. The measurement process according to claim 2, wherein after having activated the transponder module by the wake-up signal, the accelerometer or the gyroscope or the accelerometer and the gyroscope supply measurement signals to the processing unit for the transmission of measurement signals by the transmission unit to the base station for determination of a passage time over each hurdle during the race.

10. The measurement process according to claim 1, wherein following the measurement of the motion sensor or sensors on passage of two or three successive hurdles of several racing athletes, the processing unit or the base station having received the measurement signals determines placings of the athletes in real time during the race.

11. The measurement process according to claim 1, wherein following the measurement of the motion sensor or sensors on passage of a number N of hurdles, where N is a whole number higher than 1, the synchronised processing unit or the base station is able to predict final race times of each athlete to be displayed before passing through the finishing line.

12. A system for measuring or determining a time in a hurdle race of an athlete for implementing the measurement process, wherein the measurement system comprises at least one a personalised transponder module positioned on an athlete and a base station, wherein said transponder module comprises at least a signal receiver unit, a processing unit for data, measurements or commands, a transmitter unit for data and/or measurement and/or command signals, and at least one motion sensor to supply measurement signals to the processing unit, wherein the transponder module is configured to be woken up by a wake-up signal received by the receiver unit in order to enable the motion sensor to measure one or more variations in movement of the athlete on passage of one or more hurdles during the race, and in that the base station or the processing unit is arranged to determine a passage time over the hurdle or hurdles during the race and to predict, during the race, at least one of a placing of the athlete and a final race time of the athlete.

13. The measurement system according to claim 12, wherein the motion sensor is an accelerometer with one, two or three measurement axes.

14. The measurement system according to claim 12, wherein the motion sensor is a gyroscope with one, two or three measurement axes for the transponder module intended to be positioned on an upper part of the body of an athlete.

15. The measurement system according to claim 12, wherein the transponder module, which is intended to be positioned on an upper part of the body of an athlete, comprises two motion sensors, which are an accelerometer with one, two or three measurement axes and a gyroscope with one, two or three measurement axes.

16. A process for measuring or predicting a time in a hurdle race of at least one athlete by means of a personalised transponder module positioned on the athlete and a base station of a measurement system, wherein the transponder module comprises at least a signal receiver unit, a processing unit for data, measurements or commands, a transmitter unit for data and/or measurement and/or command signals, and at least one motion sensor to supply measurement signals to the processing unit, wherein the process comprises the following steps:
    activating the personalised transponder module following the receipt of a wake-up signal in the receiver unit,
    measuring at least one variation in movement of the athlete by the motion sensor on passage of one or more hurdles during the race,
    transmitting measurement signals directly or formatted with determination of variations in movement in the processing unit by the transmitter unit to the base station, and
    determining a passage time of the athlete over one or more hurdles by one or more measurements of variations in movement of the motion sensor, and
at least one of:
    (a) following the measurement of the motion sensor or sensors on passage of a number N of hurdles, where N is a whole number higher than 1, the synchronised processing unit or the base station is able to predict a final race time of each athlete to be displayed before passing through the finishing line, and
    (b) following the measurement of the motion sensor or sensors on passage of two or three successive hurdles of several racing athletes, the processing unit or the base station having received the measurement signals determines a placing of the athletes in real time during the race.

\* \* \* \* \*